(12) United States Patent
Nishihama et al.

(10) Patent No.: US 6,358,495 B1
(45) Date of Patent: Mar. 19, 2002

(54) TITANIUM-SILICA COMPLEX AND COSMETIC PREPARATION COMPOUNDING THE SAME

(75) Inventors: Shuji Nishihama; Shoichiro Shio, both of Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/534,257

(22) Filed: Mar. 24, 2000

(30) Foreign Application Priority Data

Mar. 26, 1999 (JP) .......................................... 11-083990

(51) Int. Cl.$^7$ .......................... A61K 7/42; A61K 7/021; A61K 7/025; A61K 7/035; C09C 1/36
(52) U.S. Cl. ........................ 424/59; 106/436; 106/442; 106/446; 106/481; 106/482; 424/63; 424/64; 424/69; 424/401
(58) Field of Search .................... 424/401, 59, 489, 424/63, 64, 69; 106/436, 442, 446, 481, 482

(56) References Cited

U.S. PATENT DOCUMENTS

| | | | |
|---|---|---|---|
| 3,567,480 A | | 3/1971 | Craig |
| 5,026,914 A | * | 6/1991 | Jenkins et al. ............... 564/451 |
| 5,486,354 A | | 1/1996 | Defossez et al. |
| 5,908,607 A | * | 6/1999 | Abekawa et al. ........... 423/502 |
| 6,068,824 A | * | 5/2000 | Kinoshita et al. ........ 423/239.1 |
| 6,139,614 A | * | 10/2000 | Schmid et al. ............... 106/417 |

FOREIGN PATENT DOCUMENTS

| | | | |
|---|---|---|---|
| DE | 198 02 392 A1 | | 7/1998 |
| EP | 0778319 A1 | * | 11/1997 |
| EP | 0 872 447 A1 | | 10/1998 |
| JP | 02282312 A | * | 11/1990 |
| JP | 404077417 A | * | 3/1992 |
| SU | 715595 A | * | 2/1980 |

OTHER PUBLICATIONS

Japanese Patent Office, Patent Abstracts of Japan, Publication No. 07252125 A, Date of Publication: Oct. 3, 1995, Application No. 07011582.
WO 98/14399, Date of Publication: Apr. 9, 1998, Translation of Abstract.

* cited by examiner

Primary Examiner—Jose' G. Dees
Assistant Examiner—Marina Lamm
(74) Attorney, Agent, or Firm—Ronald R. Snider; Snider & Associates

(57) ABSTRACT

To provide a complex which is excellent in transparency and protective ability of UVB region by containing titanium oxide in a specific silica carrier and a cosmetic preparation which has natural finishing i.e., excellent in transparency by the complex and is excellent in protective ability of UVB region, a titanium-silica complex in accordance with the present invention comprises a silica carrier and titanium oxide, wherein said silica carrier is mainly composed of silicon oxide and wherein titanium oxide is contained in said silica carrier.

20 Claims, 2 Drawing Sheets

TITANIUM-SILICA COMPLEX AND COSMETIC PREPARATION COMPOUNDING THE SAME

RELATED APPLICATIONS

This application claims the priority of Japanese Patent Application No. 11-83990 filed on Mar. 26, 1999, which is incorporated herein by reference.

FIELD OF THE INVENTION

The present invention relates to a titanium-silica complex and, in particular, to an improvement in properties of titanium dioxide which has ultraviolet protective ability.

BACKGROUND OF THE INVENTION

Sunburn is caused by the relation between the light of 280 to 400 nm, which reaches on the ground, among ultraviolet ray and light sensitivity of the skin. Sunscreen cosmetic preparations that comprise UV-absorber or UV-screening agent exist in order to prevent sunburn. Sunscreen cosmetic preparations can demonstrate their effect by applying them onto the skin.

In the region of ultraviolet ray which melanize the skin, the ultraviolet ray of 280 to 320 nm that is called UV-B produces erythema and also produces melanization after producing erythema. To the contrary, the ultraviolet ray of 320 to 400 nm that is called UV-A directly produces melanization without producing erythema. Some cosmetic preparation may achieve absorption and screening of such ultraviolet ray by compounding organic materials. In recent years, however, it is mainstream that the cosmetic preparations which obtain such effects by adding inorganic powders that is stable with respect to light and have small influence on the human body.

As inorganic powders, zinc oxide, titanium oxide and the like are exemplified. The refractive index of titanium oxide is 2.3 to 2.6 and is highest among pigments. Hiding power of titanium oxide is also greatest among white pigments and is two times to three times of zinc oxide. In the actual sunscreen cosmetic preparation, however, it is desirable to prevent sunburn with making the application of the inorganic powder inconspicuous.

Accordingly, the sunscreen cosmetic preparations which compound ultrafine titanium oxide that is inconspicuous in whiteness as compared with pigment class titanium oxide and which have natural finishing and excellent ultraviolet absorbing ability have been developed recently.

However, when the particle diameter of titanium dioxide is cut into smaller pieces, oil absorption is increased because of expansion of specific surface area. Consequently, dispersibility of base system in cosmetic preparation is deteriorated and ultraviolet ray transmission rate also receives bad influence.

Amelioration of dispersibility for base system and ultraviolet protective ability can be demonstrated by making titanium dioxide to spindle shape. However, it is not always found so much amelioration with respect to transparency.

SUMMARY OF THE INVENTION

The present invention is achieved in view of the foregoing problems, an object of the present invention is to provide a complex which is excellent in transparency and protective ability of UVB region by containing titanium oxide in a specific silica carrier.

Another object of the present invention is to provide a cosmetic preparation which has natural finishing i.e., excellent in transparency by the complex and is excellent in protective ability of UVB region.

In order to achieve the foregoing object, a titanium-silica complex in accordance with the present invention comprises a silica carrier and titanium oxide, wherein said silica carrier is mainly composed of silicon oxide and wherein titanium oxide is contained in said silica carrier.

Also, in the present invention, it is preferable that plurality of a fine titanium oxide particle is incorporated in said silica carrier in the dotted form that has almost homogeneous density.

Also, in the present invention, a complex of silicon oxide and titanium oxide that is obtained by including titanium oxide is preferable in case of depositing silicon oxide.

Also, in the present invention, a complex of silicon oxide and titanium oxide that is obtained by including a precursor of titanium oxide is preferable in case of depositing silicon oxide.

Also, in the present invention, a complex of silicon oxide and titanium oxide that is obtained by including titanium oxide is preferable in case of depositing a silicate.

Also, in the present invention, a complex of silicon oxide and titanium oxide that is obtained by including a precursor of titanium oxide is preferable in case of depositing a silicate.

Also, in the present invention, it is preferable that an additive concentration of titanium oxide is 0.5 to 90% with respect to the whole mass of the powder.

A cosmetic preparation in accordance with the present invention compounds any one of the titanium-silica complexes as mentioned hereinbefore.

BEST MODE FOR CARRYING OUT THE INVENTION

Figure 1:
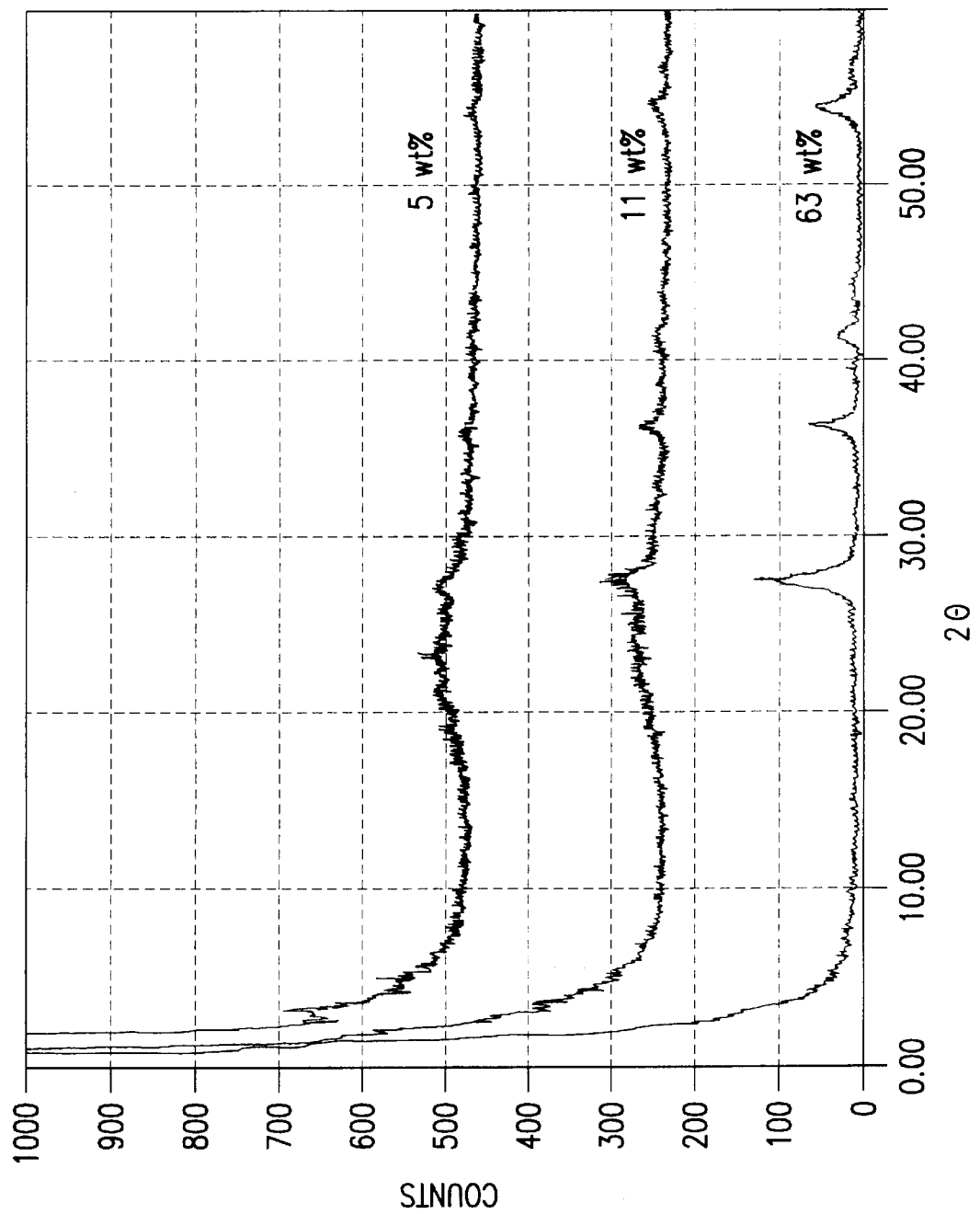
FIG. 1 is an X-ray diffraction pattern of the titanium-silica complex which has the form of fine particle mesoporous powder.

As a result of the diligent studies performed by the present inventors in order to manufacture the complex which is excellent in ultraviolet protective ability of titanium oxide and in dispersibility in base system and transparency, it has been found that titanium-silica complex which mixes a specific silica carrier and titanium oxide is useful. Accordingly, the present invention has been accomplished.

Namely, the present invention is characterized in that comprises a silica carrier and titanium oxide and said silica carrier is mainly composed of silicon oxide and titanium oxide is contained in said silica carrier.

The titanium-silica complex of the present invention is very affluent in transparency because the complex incorporates plurality of the fine titanium oxide particles in the silica carrier in the dotted form that has almost homogeneous density. Further, the titanium-silica complex is affluent in dispersibility to base as well as has excellent ultraviolet protective ability.

The general manufacturing method of the titanium-silica complex of the present invention is explained in the following.

Manufacturing Method

A first manufacturing method of the titanium-silica complex in accordance with the present invention is as follows. As the simplest manufacturing method, the method which adds a liquid that titanium oxide fine particle is dispersed to a liquid that silicon oxide fine particle is dispersed and complexes by inclusion of titanium oxide in case of depositing silicon oxide, the method which disperse titanium oxide fine particle to a liquid that silicon oxide fine particle dispersed and complexes by inclusion of titanium oxide in case of depositing silicon oxide, and the method which disperse silicon oxide fine particle to a liquid that titanium oxide fine particle dispersed and calcinates or dries with inclusion of titanium oxide in case of depositing silicon oxide are exemplified.

As the liquid that silicon oxide fine particle is dispersed, silica sol and the like are exemplified. As the liquid that titanium oxide fine particle is dispersed, titania sol and the like are exemplified. However, silicon oxide and titanium oxide for the purpose of obtaining the complex of the present invention is not restricted thereto exemplified herein.

A second manufacturing method of the titanium-silica complex in accordance with the present invention is as follows. The method is to obtain the complex of silicon oxide and titanium oxide by mixing the precursor of titanium oxide which has various forms with a liquid that silicon oxide fine particle is dispersed and calcinating or drying the inclusion of titanium oxide in case of depositing silicon oxide.

In the present invention, as examples of the precursors of titanium oxide which have various forms, titanium tetrachloride, titanium sulfate, titanyl sulfate, titanium tetra-i-propoxide (TTIP) and the like are listed. However, it is necessary to dissolve to a liquid even when the precursor has any shape. The precursor of titanium oxide for the purpose of obtaining the complex of the present invention is not restricted thereto exemplified herein.

A third manufacturing method of the titanium-silica complex in accordance with the present invention is as follows. The method is to obtain the complex of silicon oxide and titanium oxide by mixing titanium oxide which has various forms with the material that contains various silicon for depositing a silicate and by including titanium oxide and calcinating or drying it in case of depositing silicate.

As the materials for depositing silicate, the materials that contain various silicon can be used. Examples of the material that contains silicon, include a silicate, a silicon alkoxide and a water glass.

Examples of the silicate include $Na_2SiO_3$ and $Na_4SiO_4$.

Examples of the silicon alkoxide include tetramethyl orthosilicate and tetraethyl orthosilicate.

Examples of the water glass include JIS No. 1, JIS No. 2 and JIS No. 3.

The material which contains silicon for the purpose of obtaining the complex of the present invention is not restricted thereto exemplified herein.

A fourth manufacturing method of the titanium-silica complex in accordance with the present invention is as follows. The method is to obtain the complex of silicon oxide and titanium oxide by including the precursors which have various forms and calcinating or drying it in case of depositing the material which contains various silicon for depositing the silicate.

In each manufacturing method mentioned hereinbefore, the method, which add an acid or a base was exemplified in order to deposit silicon oxide or silicates and include titanium oxide or precursors thereof However, the manufacturing method is not restricted in particular as long as the method can deposit silicon oxide or silicates and include titanium oxide or precursors thereof.

In the third and fourth manufacturing methods, it is possible to manufacture the titanium-silica complex which has several forms of mesoporous powder in case of depositing silicon oxide under specific condition according to the manufacturing example of the mesoporous powder described in W098/14399. The forms of the mesoporous powder include a fine particle mesoporous powder, a rod-like mesoporous powder which characterizes in that a mesopore whose outer diameter is 20 to 200 nm elongates to longitudinal direction and a rod-like macroporous powder which hardly has a mesopore.

In this place, the manufacturing method of the titanium-silica complex of the present invention which has the form of the fine particle mesoporous powder, rod-like mesoporous powder and rod-like macroporous powder mentioned in above is explained.

Manufacturing Method of Titanium-Silica Complex Having Forms of Each Porous Powder Manufacturing method of porous powder comprises a dissolution step for dissolving a silicate, a condensation step for depositing silicic acid on a micelle and a removal step for removing surfactant.

Manufacturing method of each porous powder is explained in the following.

The fine particle mesoporous powder was obtained as follows. 0.1 to 5.0M of the silicate, which was $0<SiO_2<Y_2O<2$ (Y: alkali metal atom), was dissolved at pH 11 or more under the presence of the cationic surfactant. A rod-like micelle was formed with said cationic acid by adjusting pH to 10.5 or less while silicic acid was deposited on the rod-like micelle. The cationic acid was removed from the micelle-like deposit whose outer shell was the silicate that was formed by deposition. Thereby, yielding the fine particle mesoporous powder.

The rod-like mesoporous powder was obtained by dissolving the silicate under concentration of 0.3 to 1.3M at dissolution step and adjusting pH to 10.5 or less within 30 minutes in the manufacturing method of the fine particle mesoporous powder mentioned hereinbefore.

The rod-like macroporous powder was obtained by dissolving the silicate under concentration of 1.3 to 2.0M at dissolution step and adjusting pH to 10.5 or less within 30 minutes in the manufacturing method of the fine particle mesoporous powder mentioned hereinbefore.

In said manufacturing steps, the titanium-silica complex of the present invention which has the form of each porous powder can be obtained by adding titanium oxide solution or the precursor solution thereof at any step. It is found that the obtained titanium-silica complex remain unchanged in transparency, dispersibility to base and ultraviolet protective ability even when the titanium oxide solution or the precursor solution thereof is added at any step of dissolution step of silicate, condensation step and surfactant removal step.

As mentioned hereinbefore, it is confirmed that the titanium-silica complex which has the form of the porous powder ameliorates dispersibility of titanium particle in the silica carrier and further becomes favorable in ultraviolet screening effect in comparison to the simple mixture of silica and titanium.

Further, oil absorption becomes great because the specific surface area of the powder becomes greater than the normal silica powder owing to a mesopore or a macropore. Accordingly, it is found that cosmetic durability with time passage can be improved in the case where the titanium-silica complex of the porous powder is compounded to the cosmetic preparation.

In the present invention, the additive concentration of titanium oxide in the obtained complex is preferably 0.5 to 90 wt % and more preferably 1 to 85 wt % with respect to the whole mass of powder. If the amount of titanium oxide is 0.5 wt % or less, ultraviolet protective effect can be perceived. However it is deficient in utility. On the other hand, transparency tends to be deteriorated if the amount of titanium oxide is 90 wt % or more.

In the following, the embodiment of the present invention is further explained with referring to examples of the present invention. However, the present invention is not restricted thereto.

EXAMPLE 1

A titanium-silica complex was manufactured according to a third manufacturing method.

0.01 mol of behenyl trimethylammonium chloride (BTC) was dissolved to 100 ml of 0.5M sodium metasilicate solution. 40 ml of 15% titania sol was added thereto and the temperature at this time was 70° C. After adjusting pH to approximately 8 by the use of hydrochloric acid, the dispersion was filtered. After washing the residue with water and drying, it was calcinated at 700° C., thereby yielding the titanium-silica complex which has the form of the fine particle mesoporous powder.

EXAMPLE 2

A titanium-silica complex was manufactured according to a fourth manufacturing method.

0.01 mol of behenyl trimethylammonium chloride (BTC) was dissolved to 100 ml of 0.5M sodium metasilicate solution. Hydrochloric acid and 3 g of titanium tetrachloride as titanium oxide were added thereto so as to adjust pH to approximately 8. The temperature at this time was 70° C. Thereafter, the dispersion was filtered and the residue was washed with water and was dried. Then the residue was calcinated at 700° C., thereby yielding the titanium-silica complex which has the form of the fine particle mesoporous powder.

EXAMPLE 3

A titanium-silica complex was manufactured according to a fourth manufacturing method.

0.01 mol of stearyl trimethylammonium chloride (BTC) was dissolved to 100 ml of 0.5M sodium metasilicate solution. Hydrochloric acid and 3 g of titanyl sulfate as titanium oxide were added thereto so as to adjust pH to approximately 8. The temperature at this time was 70° C. Thereafter, the dispersion was filtered and the residue was washed with water and was dried. Then the residue was calcinated at 700° C., thereby yielding the titanium-silica complex which has the form of the fine particle mesoporous powder.

EXAMPLE 4

A titanium-silica complex was manufactured according to a fourth manufacturing method.

3 g of titanium tetra-i-propoxide (TTIP) was dissolved to 9 g of isopropyl alcohol. 2.5 g of water was added thereto so as to obtain titanium hydroxide. Thereafter, 0.01 mol of behenyl trimethylammonium chloride (BTC) was dissolved to 100 ml of 0.5M sodium metasilicate solution. The former titanium hydroxide solution was added to the latter solution. The temperature at this time was 70° C. After adjusting pH to approximately 8 by the use of hydrochloric acid, the dispersion was filtered. After washing the residue with water and drying, it was calcinated at 700° C., thereby yielding the titanium-silica complex which has the form of the fine particle mesoporous powder.

EXAMPLE 5

A titanium-silica complex was manufactured according to a first manufacturing method.

50 ml of 10% silica sol and 50 ml of 10% titania sol were mixed and stirred and the solution was left at rest under vacuum. After vacuum drying, the residue was calcinated at 700° C., thereby yielding the fine particle titanium-silica complex.

EXAMPLE 6

A titanium-silica complex was manufactured according to a second manufacturing method.

50 ml of 10% silica sol and 3 g of titanium tetrachloride solution as titanium oxide were mixed and stirred and the solution was left at rest under vacuum. After vacuum drying, the residue was calcinated at 700° C., thereby yielding the fine particle titanium-silica complex.

EXAMPLE 7

A titanium-silica complex was manufactured according to a fourth manufacturing method. 0.01 mol of behenyl trimethylammonium chloride (BTC) was dissolved to 100 ml of 0.5M sodium metasilicate solution. 40 ml of 15% titania sol was added thereto and the temperature at this time was 70° C. After adjusting pH to approximately 8 by the use of hydrochloric acid, the dispersion was filtered. After washing the residue with water and drying, it was calcinated at 700° C., thereby yielding the titanium-silica complex which has the form of the rod-like mesoporous powder.

EXAMPLE 8

A titanium-silica complex was manufactured according to a fourth manufacturing method.

0.03 mol of behenyl trimethylammonium chloride (BTC) was dissolved to 100 ml of 1.5M sodium metasilicate solution. 40 ml of 15% titania sol was added thereto and the temperature at this time was 70° C. After adjusting pH to approximately 8 by the use of hydrochloric acid, the dispersion was filtered. After washing the residue with water and drying, it was calcinated at 700° C., thereby yielding the titanium-silica complex which has the form of the rod-like macroporous powder.

In the titanium-silica complex obtained by the above-described examples, plurality of the fine titanium oxide particles exist in the silica carrier in the dotted form at specific intervals. The titanium-silica complex has high transparency. When the obtained titanium-silica complex was observed with naked eye, the color of white pigment that has high hiding property peculiar to titanium oxide was not observed. The color of the titanium-silica complex was semitransparent to white powder.

When the present inventors have examined particle size distribution of the titanium-silica complex that has the porous powder as like Examples 1 to 4, 7 and 8, the particle size was distributed within the range of 0.5 to 50 $\mu$m. Accordingly, it is possible to uniform the desired particle diameter by adjusting with a sieve and the like in the case where adjustment of the particle diameter is required.

It is also possible to control the particle diameter of the titanium-silica complex in accordance with the present invention by wet process or dry process such as pulverization as occasion demands as long as the useful effect is not spoiled.

Then, the X-ray diffraction pattern of the titanium-silica complex of the present invention, which has the form of fine particle mesoporous powder, was examined. In here, the difference of the obtained complex was examined according to the amount of titanium oxide to be contained in the silica carrier.

FIG. 1 is the X-ray diffraction pattern of the titanium-silica complex which has the form of the fine particle mesoporous powder. As a sample, three types of the sample whose content of titanium oxide was 5 wt %, 11 wt % and 63 wt % were used. It is confirmed from FIG. 1 that the pore of the titanium-silica complex which has the form of the fine particle mesoporous powder is closely related with the content of titanium oxide.

This does not mean that titanium oxide is supported by the pore of the porous powder. It seems that the addition of titanium oxide influences on the generation of the pore in the process of crystallization of the porous powder. Conversely, it is possible to adjust the surface area to some extent by using this property.

COMPARATIVE EXPERIMENT

Comparative experiment had been performed so as that what extent of transparency, ultraviolet protective ability and dispersibility in the base system of the complex of the present invention was ameliorated as compared with the conventional fine particle titanium oxide. As a sample, the powder obtained by Example 1 was used. As a comparative subject, a fine particle titanium oxide (goods on the market: manufactured by Ishihara Sangyo) whose particle diameter was 0.01 to 0.02 $\mu$m in the minor axis and 0.05 to 0.1 $\mu$m in the major axis, which had been used conventionally in ultraviolet protection, was used. Further, a fine particle mesoporous powder was manufactured without adding 15% titania sol in the step of Example 1. Said fine particle titanium oxide was adsorbed to the surface of the fine particle mesoporous powder and this was also used as the comparative subject.

Measurement of ultraviolet protective ability was performed as follows. First, the slurry of each powder and castor oil was produced by mixing Example 1, fine particle titanium oxide, titanium oxide adsorbed mesoporous powder to castor oil separately so as that the content of titanium oxide might be adjusted to 3%. Each slurry was kneaded by a three-roller separately. After kneading, a coating was formed on a silica plate by an applicator of 10 $\mu$m thickness. Ultraviolet ray transmission rate of the coating was measured by a spectrophotometer (U-3410, manufactured by Hitachi).

The mixture mixed in the prepared sample is described in Table 1.

TABLE 1

| | Mixture to Castor Oil |
|---|---|
| Example 9 | Example 1 |
| Comp. Ex. 1 | Fine Particle Titanium Oxide |
| Comp. Ex. 2 | Titanium Oxide Adsorbed Mesoporous Powder |

As shown in Table 1, Example 1•castor oil slurry, fine particle titanium oxide•castor oil slurry and titanium oxide adsorbed mesoporous powder- castor oil slurry is referred to as Example 9, Comparative Examples 1 and 2, respectively.

With regard to transparency and dispersibility, a coating was formed on black colored paper by applying Example 9, Comparative Examples 1 and 2 those were obtained in said experiment by an applicator of 10 $\mu$m thickness. The measurement was performed by visual observation.

Figure 2:
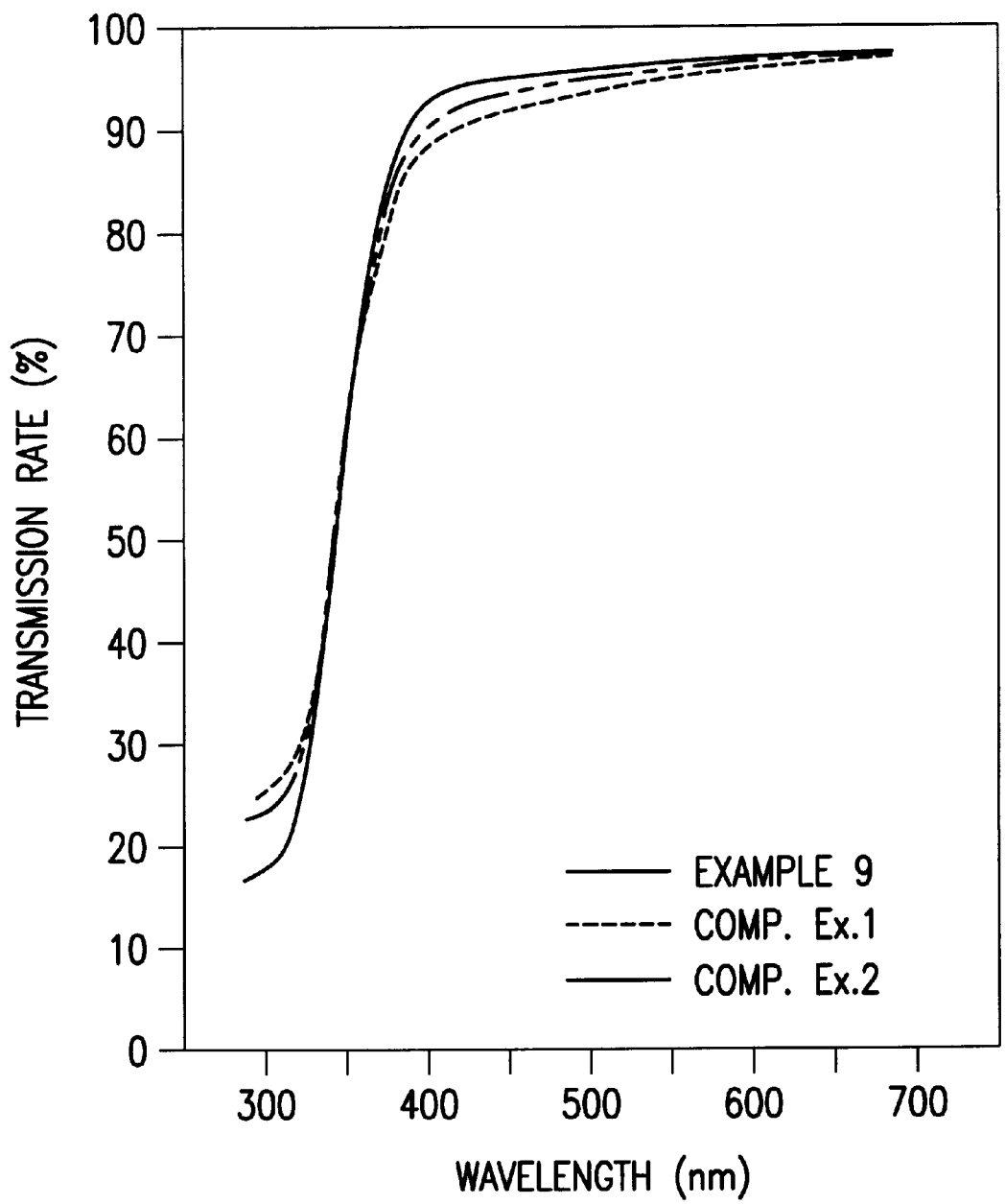
FIG. 2 is a measurement result of ultraviolet ray transmission rate in Example 9 and Comparative Examples 1 and 2.

FIG. 2 is a measurement result of ultraviolet ray transmission rate in Example 9 and Comparative Examples 1 and 2. It is understood from the result of FIG. 2 that Example 9 screens the ultraviolet ray transmission rate in UV-B region of 290 to 320 nm to 20% or less. Also, though the ultraviolet ray transmission rate in UV-A region of 320 to 400 nm was increased as the wavelength becomes longer, nevertheless Example 9 favorably screens the ultraviolet ray up to 350 nm as compared with Comparative Example 1. To the contrary, the ultraviolet ray transmission rate in UV-B region of 290 to 320 nm is 25% or more in Comparative Example 1. Though Comparative Example 1 favorably screens the ultraviolet ray in UV-A region of 350 nm or more as compared with Example 9, nevertheless the great difference is not observed in the ultraviolet ray transmission rate, Accordingly, Comparative Example 1 is considerably inferior to Example 9 on the point of the present object that is excellent in ultraviolet protective ability in UV-B region.

Transmission rate in visible area is further notable. The difference of transmission rate between Example 9 and Comparative Example 1 comes to vanish as the wavelength of the light becomes longer. In here, however, FIG. 2 shows that the transmission rate of Example 9 is higher than the one of Comparative Example 1 in the whole visible area. Accordingly, it can be observed that the titanium-silica complex of the present invention is excellent in transparency as compared with the material that merely compounds the fine particle titanium oxide.

As for Comparative Example 2, though the excellent result can be obtained in comparison to Comparative Example 1, nevertheless the properties of Comparative 2 is almost same as the ones of Comparative 1.

Then, transparency and dispersibility of each sample which is applied on black colored paper that is observed with visual observation is shown in Table 2. Evaluation method is as follows.

Transparency:
There was transparency: ⊚
Whiteness was slightly conspicuous and there was almost no transparency: Δ
Whiteness was conspicuous and there was no transparency: X
Dispersibility:
Aggregation was not perceived: ⊚
Aggregation was perceived, but density thereof was low: ΔAggregation was perceived: X

TABLE 2

| | Example 9 | Comp. Ex. 1 | Comp. Ex. 2 |
|---|---|---|---|
| Transparency | ○ | X | Δ |
| Dispersibility | ○ | X | Δ |

When Example 9 was observed, Example 9 was seen in the manner as the color of the applied surface was passed through frosted glass and transparency of the coating was remarkably observed. Further, a mass which seemed to be caused aggregation was not observed.

To the contrary, Comparative Example 1 was observed in the manner that the color of the applied surface came to the surface with white. Further it seems that Comparative Example 1 was aggregated because numerous small dot-like white particles were observed in places.

Also, Comparative Example 2 was not seen white as much as Comparative Example 1. However, Comparative Example 2 was observed in the manner that the color of the applied surface came to the surface with white. The reason is seemed as follows. The powder is coated with titanium oxide by surface adsorption with the mesoporous powder. Accordingly, the color shown by the fine particle titanium oxide was given to the whole powder and the form of the porous powder was set off by titanium oxide. Further, small dot-like white particles were also observed in places thought it was remarkably less than Comparative Example 1. The reason why seems because the fine particle titanium oxide which is separated from surface adsorption condition is aggregated in the similar manner as Comparative Example 1.

Thus it was confirmed that Example 9 which compounds the titanium-silica complex of the present invention is ameliorated in transparency, dispersibility and ultraviolet protective ability in comparison with the conventional fine particle titanium oxide.

It was also found that the effect was not obtained by simply supporting titanium oxide with surface adsorption.

In Example 9, though the complex which was obtained from Example 1 was used, almost same result was shown as like comparative experiment in the case where the same experiment was performed with respect to the complexes those were obtained from Examples 2 to 8.

As mentioned above, the titanium-silica complex of the present invention can be compounded to the various articles which require ultraviolet protective ability since it is excellent in transparency and is affluent in dispersibility to base in addition to have excellent ultraviolet protective ability. Particularly, if the titanium-silica complex was compounded to the cosmetic preparation, it can impart excellent ultraviolet protective ability and feeling of use and natural finishing to the cosmetic preparation.

The titanium-silica complex of the present invention is stable thermally and chemically because it contains titanium oxide in the silica carrier. Accordingly, in addition to the oily ingredient such as castor oil that was used in comparative experiment, it is possible to compound water, powders, surfactants, lower alcohols, polyvalent alcohols, humectants, antiseptics, high polymers, antioxidants, perfumes and various pharmaceuticals within the qualitative and quantitative range that the ultraviolet protective effect of the present invention is not spoiled.

As for the powder which can be compounded with the titanium-silica complex of the present invention, the powder generally used for the cosmetic preparation can be listed. Examples of the powder include inorganic pigments, pearl pigments, metallic flake pigments, organic pigments and natural coloring matters. However, the powder which can be used in the present invention is not restricted thereto.

As for the oily ingredient which can be compounded with the titanium-silica complex of the present invention, the oily ingredient generally used for the cosmetic preparation can be listed. Examples of the oily ingredient include liquid fats and oils, solid fats and oils, waxes, hydrocarbons, higher fatty acids, higher alcohols, ester oils and silicones. However, the oily ingredient which can be used in the present invention is not restricted thereto. Further, the oily ingredient can be used with selecting one or more of them voluntary.

As for the surfactant which can be compounded with the titanium-silica complex of the present invention, the surfactant generally used for the cosmetic preparation can be used with or without its ionicity. Examples of the surfactant include anionic surfactants, cationic surfactants, amphoteric surfactants, lipophilic nonionic surfactants and hydrophilic nonionic surfactants. However, the surfactant which can be used in the present invention is not restricted thereto. Further, the surfactant can be used with selecting one or more of them voluntary.

A shape of the cosmetic preparation which compounds the titanium-silica complex of the present invention is not restricted in particular. For example, it is possible to take the form of powder, cream, stick, pencil and liquid according to its use. Accordingly, it is possible to provide various kinds of cosmetic preparation such as make-up base, foundation, face powder, rouge, lipstick, mascara, eye shadow, eye liner, cream, milky lotion and lotion.

Titanium oxide is known to function as photocatalyst by irradiation of light, in particular, by irradiation of ultraviolet ray. In the case where titanium oxide is compounded to a certain kind of base system, it may deteriorate the other ingredient in base agent due to photocatalyst function. The present invention can inhibit such photocatalyst activity in certain degree by complexing the silica carrier and titanium oxide. Therefore, the present invention can inhibit photocatalyst function of titanium oxide and avoid the problems caused by photocatalyst function even if anatase titanium oxide is used.

However, it is very useful to use rutile titanium oxide in view of deterioration of the other ingredient because rutile type titanium oxide has low activity as photocatalyst. Accordingly, it is preferable that the crystal form of titanium oxide to be complexed in the present invention is amorphous or rutile.

The cosmetic preparation that compounds the titanium-silica complex of the present invention is explained in the following. The unit of a numerical value, which is shown in the formulation, is wt %.

Formulation Example 1

O/W Emulsion Type Sunscreen

| | |
|---|---|
| 1. Titanium-Silica Complex of The Present Invention | 10 |
| 2. Zinc Oxide | 5 |
| 3. Stearic Acid | 2 |
| 4. Cetyl Alcohol | 1 |
| 5. Petroleum | 5 |
| 6. Silicone Oil | 2 |
| 7. Liquid Paraffin | 10 |
| 8. Glyceryl Monostearate (Self-Emulsion Type) | 1 |
| 9. Polyoxyethylene (25 mol) Monooleate | 1 |
| 10. Polyethylene Glycol 1500 | 5 |
| 11. Bee gum | 0.5 |
| 12. Purified Water | 57.5 |
| 13. Perfume | Q.S. |
| 14. Antiseptic | Q.S. |

Polyethylene glycol was added to purified water and the mixture was heated and dissolved. After zinc oxide and bee gum were added thereto, the mixture was dispersed homogeneously with a homomixer and the temperature was kept at 70° C. (Water Phase). The other ingredients were mixed, heated and dissolved while keeping temperature at 70° C. (Oil Phase). Oil Phase was added to Water Phase and the mixture was emulsified and dispersed homogeneously with a homomixer. After emulsifying, the emulsion was cooled down to 35° C. while stirring. Thereby, an O/W emulsion type sunscreen was obtained.

Organoleptic test was performed by 10 persons of professional panel by the use of the obtained sunscreen. The evaluation that the sunscreen was favorable in feeling of use and the color thereof suits to the skin was obtained. Sunburn protective effect was also tested by using the sunscreen for several days. The evaluation that the sunscreen was favorable without sunburn was obtained.

Formulation Example 2

Oil Type Suntan Cosmetic Preparation

| | |
|---|---|
| 1. Titanium-Silica Complex of The Present Invention | 1.5 |
| 2. Liquid Paraffin | 61.5 |
| 3. Olive Oil | 37 |
| 4. Perfume | Q.S. |
| 5. Antioxidant | Q.S. |

The ingredients were mixed and stirred sufficiently, thereby the oil type suntan cosmetic preparation was obtained. In the case where organoleptic test was performed, the favorable evaluation that the suntan cosmetic preparation was excellent in feeling of use, the skin can be tanned beautifully without producing erythema due to sunburn, and the color of the cosmetic preparation suits to the skin, was obtained.

Formulation Example 3

Powdery Foundation

| | |
|---|---|
| 1. Titanium-Silica Complex of The Present Invention | 12 |
| 2. Titanium Oxide Coated Mica | 6 |
| 3. Talc | 15 |
| 4. Sericite | 25 |
| 5. Iron Oxide | 5 |
| 6. Spherical Nylon Powder | 2 |
| 7. Spherical PMMA Powder | 4 |
| 8. Boron Nitride Powder | 1 |
| 9. Mica | Balance |
| 10. Polyether Modified Silicone | 0.5 |
| 11. Sorbitan Sesquiisostearate | 1 |
| 12. Liquid Paraffin | 3 |
| 13. Dimethyl Polysiloxane | 1 |
| 14. Petroleum | 2 |
| 15. 2-Ethylhexyl 4-Methoxycinnamate | 2 |
| 16. Glyceryl Triisooctanoate | 0.5 |
| 17. Antiseptic | Q.S. |
| 18. Perfume | Q.S. |

The ingredients 1 to 9 were mixed homogeneously. The ingredients 10 to 18 were heated and dissolved. The latter was added to the former and the mixture was mixed homogeneously again. The powdery foundation was prepared by filling the resultant to a container. In the case where organoleptic test was performed by the use of the powdery foundation, the evaluation that the foundation renders nearly the skin color, is excellent in feeling of use and has high effect for preventing sunburn, was obtained.

Formulation Example 4

Lipstick

| | |
|---|---|
| 1. Titanium-Silica Complex of The Present Invention | 8 |
| 2. Titanium Oxide Coated Mica | 4 |
| 3. Carnauba Wax | 1 |

-continued

Formulation Example 4

Lipstick

| | |
|---|---|
| 4. Candelilla Wax | 2 |
| 5. Ceresine | 10 |
| 6. Glyceryl Triisooctanoate | 9 |
| 7. Glyceryl Diisostearate | 13 |
| 8. Dimethyl Polysiloxane (Viscosity: 90,000 mPa · s at 25° C.) | 5 |
| 9. Dimethyl Polysiloxane (Viscosity: 10 mPa · s at 25° C.) | 5 |
| 10. Silicone Resin | 8 |
| 11. Squalane | Balance |
| 12. Hydroxypropyl-β-Cyclodextrin | 1 |
| 13. Macadamia Nut Fatty Acid Cholesteryl | 3.5 |
| 14. Synthetic Sodium Magnesium Silicate | 0.5 |
| 15. Hydrophobic Silica | 0.5 |
| 16. Purified Water | 2 |
| 17. Coloring Agent | Q.S. |
| 18. Antiseptic | Q.S. |
| 19. Perfume | Q.S. |

The ingredients 14 and 15 were added to the ingredient 13 which was heated up to 60° C. The ingredients 12 and a part of 16 which were dissolved homogeneously was added thereto and the mixture was stirred sufficiently. The mixture was added to the ingredients 3 to 11 that was heated and dissolved separately and the mixture was stirred sufficiently. The ingredients 1, 2 and a rest of 16 to 18 were added thereto and the mixture was stirred and dispersed. Thereafter, the lipstick was obtained by filling the resultant to a container. The lipstick obtained by Formulation Example 4 had excellent ultraviolet protective effect.

As mentioned hereinbefore, it is possible to provide the titanium-silica complex which is excellent in transparency, dispersibility to base and protective ability of UVB region according to the present invention.

The cosmetic preparation of the present invention has excellent ultraviolet protective ability by containing the titanium-silica complex.

What is claimed is:

1. A titanium-silica complex comprising a plurality of fine titanium oxide particles incorporated into a silica carrier, wherein said silica carrier is mainly composed of silicon oxide and wherein said plurality of fine titanium oxide particles is deflocculated in said silica carrier.

2. The titanium-silica complex according to claim 1, wherein said plurality of fine titanium oxide particles is deflocculated at almost homogeneous density in said silica carrier.

3. The titanium-silica complex according to claim 1, wherein said complex is obtained by complexing (a) a silica-containing substance which can produce said silica carrier with (b) titanium oxide or its precursor capable of complexing with said silica carrier so as to form said complex.

4. The titanium-silica complex according to claim 3, wherein:
 (a) said silica-containing substance is selected from the group consisting of silicon oxide, silica, water glass, silicon alkoxides and alkali metal silicates;
 (b) said titanium oxide is selected from the group consisting of amorphous titanium oxide, rutile titanium oxide, and mixtures thereof; and
 (c) said precursor of titanium oxide is selected from the group consisting of hydrates, oxides and salts of titanium.

5. The titanium-silica complex according to claim 4, wherein said complex is obtained by complexing said silicate with titanium oxide.

6. The titanium-silica complex according to claim 4, wherein said complex is obtained by complexing said silicate with said precursor of titanium oxide.

7. The titanium-silica complex according to claim 1, wherein the amount of titanium oxide is from 0.5 to 90% of the total weight of said complex.

8. A cosmetic preparation comprising the titanium-silica complex of claim 1.

9. A transparent-ultraviolet-light-absorbing titanium-silica complex having a transmission value lower than 20% in the ultraviolet B (UV-B) wavelength region of light and a transmission value greater than 90% in the visible wavelength region of light, said ultraviolet B (UV-B) wavelength region of light and said visible wavelength region of light ranging from 280 to 320 nm and from about 400 to about 5000 nm, respectively, said complex consisting essentially of a silica carrier mainly composed of silicon oxide and a plurality of fine titanium oxide particles being deflocculated at almost homogeneous density in said silica carrier; said complex having substantially inhibited the photocatalytic activity of titanium oxide.

10. The titanium-silica complex according to claim 9, wherein said complex is obtained by complexing (a) a silica-containing substance which can produce said silica carrier and (b) titanium oxide or its precursor capable of complexing with said silica carrier so as to form said complex.

11. The titanium-silica complex according to claim 10, wherein:

(a) said silica-containing substance is selected from the group consisting of silicon oxide, silica, water glass, silicon alkoxides and alkali metal silicates;

(b) said titanium oxide is selected from the group consisting of amorphous titanium oxide, rutile titanium oxide, and mixtures thereof; and (c) said precursor of titanium oxide is selected from the group consisting of hydrates, oxides and salts of titanium.

12. The titanium-silica complex according to claim 9, wherein said complex is prepared by a method comprising the steps of mixing and stirring a silica sol with a titanium oxide sol and then drying and calcining the resulting product.

13. The titanium-silica complex according to claim 9, wherein the amount of titanium oxide is from 0.5 to 90% of the total weight of said complex.

14. The titanium-silica complex according to claim 9, wherein said complex is the form of a powder.

15. The titanium-silica complex according to claim 14, wherein said powder is a mesoporous powder being selected from the group consisting of a fine particle mesoporous powder, a rod-like mesoporous powder and a rod-like macroporous powder.

16. A cosmetic preparation comprising the titanium-silica complex of claim 9.

17. The cosmetic composition according to claim 16, wherein said composition is in the form of a make-up base, a foundation, a facial powder, a mascara, an eye-shadow, an eye-liner, a lipstick, a rouge, a cream or a lotion.

18. A method of forming a transparent-ultraviolet-light-absorbing titanium-silica complex having a transmission value lower than 20% in the ultraviolet B (UV-B) wavelength region of light and a transmission value greater than 90% in the visible wavelength region of light, said method comprising the steps of complexing a silica-containing substance which can produce a silica carrier mainly composed of silicon oxide with titanium oxide or its precursor capable of forming with said silica carrier said complex and then drying and calcining the product of the complexing step.

19. The method as recited in claim 18, wherein:

(a) said silica-containing substance is selected from the group consisting of silicon oxide, silica, water glass, silicon alkoxides and alkali metal silicates;

(b) said titanium oxide is selected from the group consisting of amorphous titanium oxide, rutile titanium oxide, and mixtures thereof; and (c) said precursor of titanium oxide is selected from the group consisting of hydrates, oxides and salts of titanium.

20. The method as recited in claim 18, wherein the silica-containing substance is a silica sol and said titanium oxide is in the form of a titanium oxide sol and wherein the complexing step comprises mixing and stirring said silica sol with said titanium oxide sol.

* * * * *